US006514666B1

United States Patent
Choi et al.

(10) Patent No.: US 6,514,666 B1
(45) Date of Patent: Feb. 4, 2003

(54) PHOTORESIST MONOMERS, POLYMERS THEREOF AND PHOTORESIST COMPOSITIONS CONTAINING IT

(75) Inventors: Jae Hak Choi, Kyoungki-do (KR); Myoung Soo Kim, Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 23 days.

(21) Appl. No.: 09/703,763

(22) Filed: Nov. 1, 2000

(30) Foreign Application Priority Data

Nov. 5, 1999 (KR) .............................. 99-48702

(51) Int. Cl.[7] .......................... G03F 7/00; C07D 211/30
(52) U.S. Cl. .................... 430/270.1; 430/322; 430/905; 430/910; 549/274; 526/285
(58) Field of Search .............................. 430/270.1, 322, 430/905, 910; 549/274; 526/285

(56) References Cited

U.S. PATENT DOCUMENTS

| | | | | |
|---|---|---|---|---|
| 4,613,671 A | * | 9/1986 | Relenyi et al. .............. | 549/274 |
| 5,538,666 A | * | 7/1996 | Jin ......................... | 252/299.01 |
| 5,616,669 A | * | 4/1997 | Jin et al. ..................... | 526/285 |
| 2002/0012879 A1 | * | 1/2002 | Choi ........................ | 430/283.1 |

FOREIGN PATENT DOCUMENTS

FR             2650588 A   *   2/1991   ......... C07D/207/04

OTHER PUBLICATIONS

Jin, Sung Ho; Choi, Hyun Nam; Choi, Sam Kwon "Cyclopolymerization of dipropargyl isopropylidene malonate and characterization of the product", Journal of Polymer Science Part A: Polymer Chemistry 1993 32 (1) pp. 69–74.*

Yamamoto et al. "Cp*Ru(cod)Cl–catalyzed [2+2+2] Cycloaddition of 1,6–Heptadiynes with Allylic Ethers. A DEcisive Role of Coordinatrion to the Ether Oxygen Atom" (abstract), Journal of Organic Chemistry 1998 63 (26) pp. 9610–9611. CASREACT 130:124948.*

* cited by examiner

Primary Examiner—Janet Baxter
Assistant Examiner—Yvette M. Clarke
(74) Attorney, Agent, or Firm—Townsend and Townsend and Crew LLP

(57) ABSTRACT

The present invention provides photoresist monomers, and photoresist polymers comprising the same. In one aspect of the present invention, the photoresist monomer of the present invention is dipropargyl malonic acid cyclic isopropylidene ester of the formula:

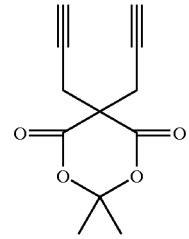

Photoresist compositions comprising the photoresist polymers of the present invention have superior 157 nm wavelength transmittance, etching resistance, heat resistance and adhesiveness. In addition, photoresist compositions of the present invention can be developed easily in 2.38 wt % aqueous TMAH solution, and therefore are suitable for lithography processes using a 157 nm wavelength-light source for fabricating a minute circuit of a high integration semiconductor device.

20 Claims, 1 Drawing Sheet

PHOTORESIST MONOMERS, POLYMERS THEREOF AND PHOTORESIST COMPOSITIONS CONTAINING IT

BACKGROUND OF THE INVENTION

1. Field of the Invention

The present invention relates to photoresist monomers, polymers derived therefrom, and photoresist compositions comprising the polymers. In particular, the present invention relates to dipropargyl malonic acid cyclic isopropylidene ester photoresist monomer, polymers and compositions suitable for photolithography processes employing KrF, ArF, EUV, and preferably 157 nm light sources like VUV.

2. Description of the Background Art

Recently, chemical amplification-type deep ultraviolet (DUV) photoresists have been investigated in order to achieve high sensitivity in minute image formation processes for preparing semiconductor devices. Such photoresists are prepared by blending a photoacid generator and a matrix resin polymer having an acid labile group.

In a photolithography process, exposure of a photoresist to light of a particular wavelength generates an acid from the photoacid generator that is present in the photoresist. This acid causes the main chain or the branched chain of the resin to decompose or become cross-linked. In addition, the acid removes the acid labile group and changes the polarity of the photoresist in the exposed region. This polarity change creates a solubility difference between the exposed portion and the unexposed portion in a developing solution, thereby allowing a pattern formation. The resolution of the pattern that is formed depends on the wavelength of the light source, i.e., in general a shorter wavelength allows formation of more minute patterns.

In general, a useful photoresist (hereinafter, abbreviated as "PR") has a variety of desired characteristics, such as an excellent etching resistance, heat resistance and adhesiveness. In addition, a photoresist should be easily developable in a commercially readily available developing solution, such as 2.38% aqueous tetramethylammonium hydroxide (TMAH) solution. Furthermore, it should provide a good pattern formation using a 157 nm wavelength light source. However, it is difficult to synthesize a photoresist polymer that satisfies all of these desired characteristics. For example, polymers having a polyacrylate polymer backbone are readily available, but they have a poor etching resistance, difficult to develop, and difficult to obtain a good minute pattern due to its poor transmittance at wavelength of 157 nm.

SUMMARY OF THE INVENTION

It is an object of the present invention to provide photoresist monomers having an excellent transmittance at 157 nm wavelength, etching resistance, adhesiveness and photosensitivity.

Another object of the present invention is to provide PR polymers derived from such photoresist monomers and methods for preparing the same.

Yet another object of the present invention is to provide photoresist compositions comprising such PR polymers.

Still another object of the present invention is to provide a semiconductor device produced by using the above described PR composition.

DETAILED DESCRIPTION OF THE INVENTION

Figure 1:
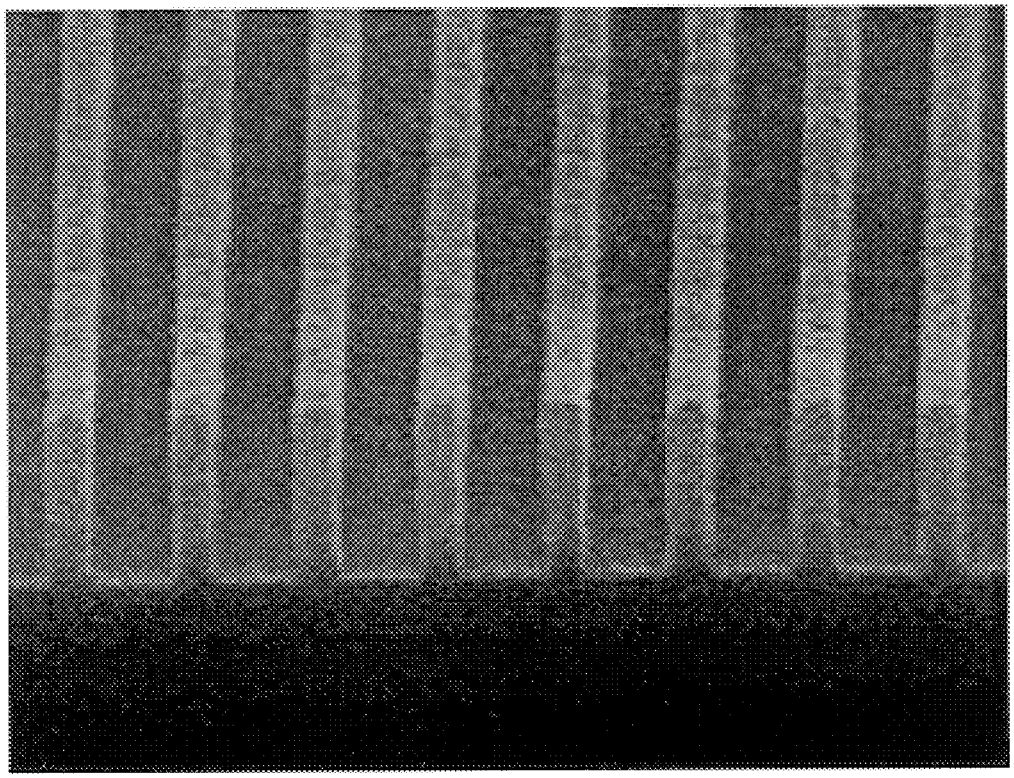
FIG. 1 shows a photoresist pattern obtained in Example 1.

The present invention provides novel photoresist monomers, which achieve the above-stated objectives. The present invention also provides photoresist polymers derived from such photoresist monomers, and a process for preparing the same. The present invention also provides a photoresist composition comprising such a PR polymer and a semiconductor device fabricated by using such a PR composition.

In one particular aspect, the present invention provides dipropargyl malonic acid cyclic isopropylidene ester (i.e., 2,2-dimethyl-5,5-dipropargyl-1,3-dioxane-4,6-dione or dipropargyl Meldrum's acid) photoresist monomer of the Formula:

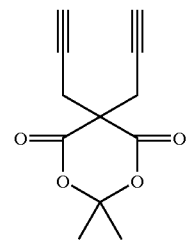

The present invention also provides a photoresist polymer derived from Compound of Formula 1, i.e., comprising dipropargyl malonic acid cyclic isopropylidene ester as a first monomer.

The photoresist polymer can further comprise a second monomer. In one particular embodiment of the present invention, the second monomer is dipropargyl carbinol of the Formula:

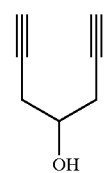

One particularly preferred photoresist polymer is of the formula:

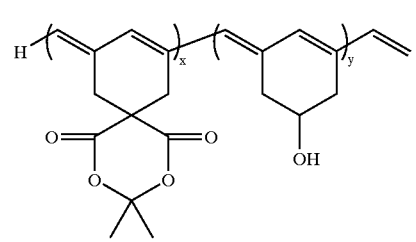

where the ratio of x:y is 0.01–100 mol %: 0–99.99 mol %.

It should be appreciated that the order of each monomeric units represented in a polymer formula of the present invention does not necessarily indicate the actual order of such monomeric units in the actual polymer. The monomeric units represented in the polymer formula is simply intended to indicate the presence of such monomeric unit in the polymer, i.e., when the variable x or y is not 0. Moreover, the variables x and y represent the total relative ratio of each units. For example, the total amount "x" of polymeric units derived from dipropargyl malonic acid cyclic isopropylidene ester may be inter dispersed throughout the polymer (not necessarily in same concentrations) or all or majority of such polymeric unit may be concentrated in one particular location of the polymer.

Preferably, the molecular weight of photoresist polymer 3 is from 3,000 to 100,000.

Polymers of the present invention can be prepared by any of the methods known to one of ordinary skill in the art, including by a metathesis polymerization of monomers with a metathesis catalyst. An exemplary process for preparing a polymer of the present invention includes the steps of admixing a metathesis catalyst and a photoresist monomer under conditions sufficient to produce the polymer. Preferably, the process further includes dissolving the metathesis catalyst in an organic solvent to produce a catalyst solution. The catalyst solution is then added to a polymerization solvent. After at a temperature of 20 to 40° C. for 10 to 20 minutes, a photoresist monomer is then added to the resulting polymerization solvent. The resulting reaction mixture is then typically heated to produce the polymer.

As stated above, the monomer can be dipropargyl malonic acid cyclic isopropylidene ester of Formula 1 or a mixture of dipropargyl malonic acid cyclic isopropylidene ester and dipropargyl carbinol of Formula 2.

The process can also include adding a cocatalyst (preferably as a cocatalyst solution) to the polymerization solvent.

A transition metal-halide or an organometallic compound can be used as the metathesis catalyst or the cocatalyst. Preferably, a catalyst is selected from the group consisting of $MoCl_5$, $WCl_6$, $Mo(OEt)_5$ and $PdCl_2$. Preferably, a cocatalyst is selected from the group consisting of $(n-Bu)_4Sn$ and $EtAlCl_2$.

The polymerization solvent is preferably selected from the group consisting of chlorobenzene, 1,4-dioxane, dimethylformamide, cyclohexane, tetrachloromethane and tetrahydrofuran. An organic solvent for producing a catalyst solution or a cocatalyst solution is preferably selected from the group consisting of hexane, tetrahydrofuran and cyclohexane.

The present invention also provides a photoresist composition comprising a photoresist polymer (i.e., photoresist resin) of Formula 3, an organic solvent and a photoacid generator.

Preferred photoacid generators include sulfides and onium type compounds. In one particular embodiment of the present invention, the photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate and dibutylnaphthylsulfonium triflate. Typically, the amount of photoacid generator used is from about 0.01% by weight to about 10% by weight of the photoresist resin employed. It has been found that when the photoacid generator is used in the amount less than about 0.01%, it lowers photosensitivity of the PR composition, and when the photoacid generator is used in the amount greater than about 10%, it results in a poor pattern formation due to its high absorption of DUV light.

Exemplary organic solvents suitable in PR compositions of the present invention include propylene glycol methyl ether acetate, ethyl lactate, methyl 3-methoxypropionate, ethyl 3-ethoxypriopionate and cyclohexanone. The amount of solvent used is preferably in the range of from about 100% to about 1000% by weight of the PR polymer. This ratio has been found to be particularly useful in obtaining a photoresist layer of a desirable thickness when coated on to a suitable substrate such as a silicon wafer in production of a semiconductor element. In particular, it has been found by the present inventors that when the amount of organic solvent is about 500% by weight of the photoresist polymer, a photoresist layer having 0.5 $\mu$m of thickness can be obtained.

The PR composition prepared by the present invention has an excellent transmittance at 157 nm wavelength, etching resistance, adhesiveness and heat resistance.

Another embodiment of the present invention provides a method for forming the PR pattern comprising (a) coating a photoresist composition described above on a substrate of semiconductor element to form a photoresist film; (b) exposing the photoresist film to light using a light source; and (c) developing the photoresist film, for example, using an alkaline solution such as 2.38 wt % TMAH solution. Optionally, the photoresist film can be heated (i.e., baked), preferably to temperature in the range of from about 70° C. to about 200° C., before and/or after the step (b).

Exemplary light sources which are useful for forming the PR pattern include VUV (157 nm), ArF (193 nm), KrF (248 nm), EUV (13 nm), E-beam, X-ray and ion beam. Preferably, the irradiation energy is in the range of from about 1 $mJ/cm^2$ to about 100 $mJ/cm^2$.

The present invention also provides a semiconductor device, which is manufactured using the photoresist composition described above.

Additional objects, advantages, and novel features of this invention will become apparent to those skilled in the art upon examination of the following examples thereof, which are not intended to be limiting.

Preparation of Photoresist Monomers

EXAMPLE 1

Synthesis of dipropargyl malonic acid cyclic isopropylidene ester

To a 300 ml of acetone was added 15 g of malonic acid cyclic isopropylidene ester (i.e., Meldrum's acid), and 34.5 g of potassium carbonate. To this solution was slowly added a solution of 33 g of propargyl bromide in 50 ml of acetone. The resulting reaction mixture was refluxed for 24 hours. The resultant solution was concentrated and recrystallized using methanol to obtain a pure dipropargyl malonic acid cyclic isopropylidene ester of Formula 1 (yield: 81%, 18 g).

EXAMPLE 2

Synthesis of dipropargyl carbinol

A Grignard reagent was prepared using 1.22 mole of magnesium and 1.49 mole of propargyl bromide. To this Grignard reagent was added 0.5 mole of ethyl formate at −5° C., and the mixture was stirred for 30 minutes. The reaction mixture was quenched by adding saturated $NH_4Cl$ aqueous solution and extracted with ethyl ether. The organic layer was fractionally distilled under reduced pressure to remove ethyl ether to obtain the compound of Formula 2 (yield:52%, 68 g).

Preparation of Photoresist Polymers

EXAMPLE 3

Synthesis of poly(dipropargyl malonic acid cyclic isopropylidene ester)

To a 100-mL flask was added 10 ml of 1,4-dioxane and 5 mM of MoCl$_5$ solution. After 15 minutes at 30° C. under nitrogen atmosphere, 55.05 g of dipropargyl malonic acid cyclic isopropylidene ester obtained using the procedure of Example 1 was slowly added and polymerized at 60° C. for 24 hours. The polymerization reaction was stopped by adding a small amount of methanol. The resultant polymer was dissolved in chloroform and precipitated in methanol. The precipitate was filtered, washed, and dried to obtain 52.3 g of the title polymer (yield 95%).

EXAMPLE 4

Synthesis of poly(dipropargyl malonic acid cyclic isopropylidene ester/dipropargyl carbinol)

The procedure of Example 3 was repeated except that a mixture of 27.53 g of dipropargyl malonic acid cyclic isopropylidene ester and 13.52 g of dipropargyl carbinol was used instead of 55.05 g of dipropargyl malonic acid cyclic isopropylidene ester, to obtain 36.95 g of the title polymer (yield: 90%).

Synthesis of Photoresist Compositions and Pattern Formation Thereof

EXAMPLE 5

A photoresist composition was prepared by adding by adding 10 g of the polymer prepared in Example 3 and 0.2 g of triphenylsulfonium triflate to 50 g of propylene glycol methyl ether acetate and filtering the resultant solution through a 0.1 µm filter.

The photoresist composition was spin-coated on a silicon wafer. The coated wafer was soft-baked at 90° C. for 90 seconds, exposed to light using an ArF exposer, post-baked at 110° C. for 90 seconds, and developed in the 2.38 wt % TMAH developing solution to obtain a ultrafine pattern of 0.15 µm L/S (see FIG. 1).

EXAMPLE 6

The procedure of Example 5 was repeated using the polymer of Example 4 instead of the polymer of Example 3 to obtain the pattern of 0.20 µm L/S.

Photoresist compositions of the present invention have excellent transmittance at wavelength of 157 nm, and. In addition, PR compositions of the present invention have an excellent etching resistance and heat resistance. Moreover, PR compositions of the present invention have excellent adhesiveness to a wafer. PR compositions of the present invention can be easily developed in 2.38 wt % aqueous TMAH solution. Therefore, photoresist compositions of the present invention can be advantageously used as a 157 nm wavelength photoresist layer in a semiconductor device. Since photoresist compositions of the present invention have a good adhesiveness, a satisfactory depth of focus (DOF) can be achieved. Consequently, a reliable high integration semiconductor device can be manufactured using photoresist compositions of the present invention.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A photoresist polymer derived from a photoresist monomer comprising a compound of the formula:

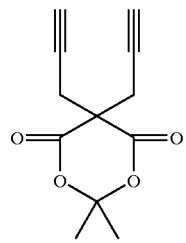

and a compound of the formula:

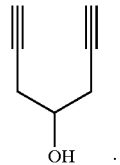

2. The photoresist polymer according to claim 1, wherein said polymer is of the formula:

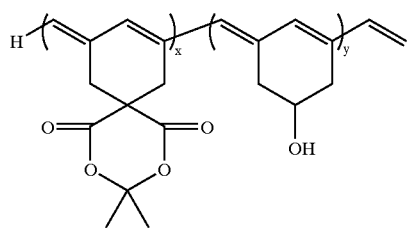

wherein, the ratio of x:y is 0.01–99.99 mol %:0.01–99.99 mol %.

3. The photoresist polymer according to claim 1, wherein the molecular weights of said photoresist polymer is in the range of from about 3,000 to about 100,000.

4. A process for preparing a photoresist polymer comprising the steps of admixing a metathesis catalyst and a photoresist monomer under conditions sufficient to produce said photoresist polymer, wherein said photoresist monomer comprises a compound of the formula:

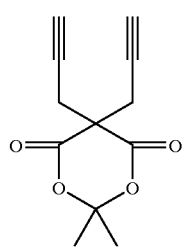

and a compound of the formula:

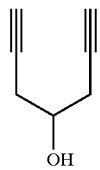

5. The process according to claim 4, wherein said metathesis catalyst comprises a catalyst and a cocatalyst.

6. The process according to claim 5, wherein each of said catalyst and cocatalyst is independently a transition metal-halide or an organometallic compound.

7. The process according to claim 6, wherein said catalyst is selected from the group consisting of MoCl$_5$, WCl$_6$, Mo(OEt)$_5$ and PdCl$_2$; and said cocatalyst is selected from the group consisting of (n-Bu)$_4$Sn and EtAlCl$_2$.

8. The process according to claim 5, wherein said catalyst further comprises a catalyst solvent and said cocatalyst further comprises a cocatalyst solvent, wherein each of said catalyst solvent and said cocatalyst solvent is independently selected from the group consisting of hexane, tetrahydrofuran and cyclohexane.

9. The process according to claim 4, wherein said admixture further comprises a polymerization solvent selected from the group consisting of chlorobenzene, 1,4-dioxane, dimethylformamide, cyclohexane, tetrachloromethane and tetrahydrofuran.

10. A photoresist composition comprising an organic solvent, a photoacid generator, and a photoresist polymer of the formula:

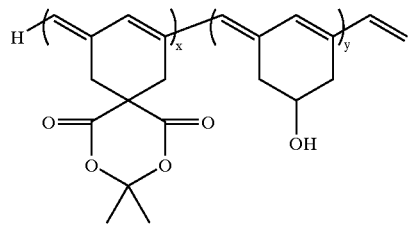

wherein, the ratio of x:y is 0.01–100 mol %:0–99.99 mol %.

11. The photoresist composition according to claim 10, wherein said photoacid generator is one or more compounds selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluoroantimonate, triphenylsulfonium triflate and dibutylnaphthylsulfonium triflate.

12. The photoresist composition according to claim 10, wherein the amount of said photoacid generator is in the range of from about 0.1 to about 10% by weight of said photoresist polymer employed.

13. The photoresist composition according to claim 10, wherein said organic solvent is selected from a group consisting of methyl ether acetate, propylene glycol methyl ether acetate, ethyl lactate, methyl 3-methoxypropionate, ethyl 3-ethoxypriopionate and cyclohexanone.

14. The photoresist composition according to claim 10, wherein the amount of organic solvent is in the range from about 100 to about 1000% by weight of said photoresist polymer employed.

15. A process for forming a photoresist pattern comprising the steps of:

(a) coating a photoresist composition on a substrate of semiconductor element to form a photoresist film, wherein said photoresist composition comprises an organic solvent, a photoacid generator, and a photoresist polymer of the formula:

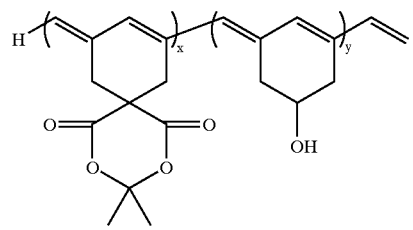

wherein, the ratio of x:y is 0.01–100 mol %:0.01–99.99 mol %;

(b) exposing said photoresist film to light using a light source; and (c) developing said photoresist film.

16. The process according to claim 15, further comprising a baking step before and/or after said exposure step (b).

17. The process according to claim 16, wherein said baking step is performed at a temperature range of from about 70 to about 200° C.

18. The process according to claim 15, wherein said light source is VUV, ArF, KrF, EUV, E-beam, X-ray or ion beam.

19. The process according to claim 15, wherein said photoresist film is irradiated with light-exposure energy in the range of from about 1 to about 100 mJ/cm$^2$.

20. A semiconductor element manufactured by the process according to claim 15.

* * * * *

UNITED STATES PATENT AND TRADEMARK OFFICE
CERTIFICATE OF CORRECTION

PATENT NO.    : 6,514,666 B1
DATED         : February 4, 2003
INVENTOR(S)   : Jae Hak Choi and Myoung Soo Kim It is certified that error appears in the above-identified patent and that said Letters Patent is hereby corrected as shown below:

<u>Column 8,</u>
Lines 39-40, the phrase "wherein, the ratio of x:y is 0.01-100 mol %:0.01-99.99 mol %;" should read -- wherein, the ratio of x:y is 0.01-100 mol %:0-99.99 mol %; --.

Signed and Sealed this

Second Day of March, 2004

JON W. DUDAS
*Acting Director of the United States Patent and Trademark Office*